(12) United States Patent
Zhang et al.

(10) Patent No.: US 11,247,996 B2
(45) Date of Patent: Feb. 15, 2022

(54) SMALL MOLECULE INHIBITORS FOR TRANSCRIPTION FACTORS

(71) Applicants: University of Massachusetts, Boston, MA (US); University of Rochester, Rochester, NY (US)

(72) Inventors: Wei Zhang, Boston, MA (US); Jian Zhu, Boston, MA (US)

(73) Assignees: University of Massachusetts, Boston, MA (US); University of Rochester, Rochester, NY (US)

( * ) Notice: Subject to any disclaimer, the term of this patent is extended or adjusted under 35 U.S.C. 154(b) by 482 days.

(21) Appl. No.: 16/321,589

(22) PCT Filed: Jul. 28, 2017

(86) PCT No.: PCT/US2017/044494
§ 371 (c)(1),
(2) Date: Jan. 29, 2019

(87) PCT Pub. No.: WO2018/023060
PCT Pub. Date: Feb. 1, 2018

(65) Prior Publication Data
US 2021/0284643 A1    Sep. 16, 2021

Related U.S. Application Data

(60) Provisional application No. 62/368,733, filed on Jul. 29, 2016.

(51) Int. Cl.
*C07D 487/04*  (2006.01)
*A61P 31/18*   (2006.01)
*A61P 35/00*   (2006.01)
*A61K 45/06*   (2006.01)

(52) U.S. Cl.
CPC ............ *C07D 487/04* (2013.01); *A61K 45/06* (2013.01); *A61P 31/18* (2018.01); *A61P 35/00* (2018.01)

(58) Field of Classification Search
None
See application file for complete search history.

(56) References Cited

U.S. PATENT DOCUMENTS

2016/0168154 A1    6/2016    Marineau et al.

FOREIGN PATENT DOCUMENTS

WO    WO2015/013635       1/2015
WO    WO 2016/201370 A1 * 12/2016 .......... C07D 401/14

OTHER PUBLICATIONS

Bosque et al., "Studies of HIV-1 latency in an ex vivo model that uses primary central memory T cells," Methods, Jan. 1, 2011, 53(1):54-61.
Bouchat et al., "Histone methyltransferase inhibitors induce HIV-1 recovery in resting CD4+ T cells from HIV-1-infected HAART-treated patients," Aids, Jul. 31, 2012, 26(12):1473-82.
Darcis et al.. "An in-depth comparison of latency-reversing agent combinations in various in vitro and ex vivo HIV-1 latency models identified bryostatin-1+ JQ1 and ingenol-B+ JQ1 to potently reactivate viral gene expression," PLoS Pathog, Jul. 30, 2015, 11(7):e1005063, 1-36.
Huang et al.. "FACT proteins, SUPT16H and SSRP1, are transcriptional suppressors of HIV-1 and HTLV-1 that facilitate viral latency," Journal of Biological Chemistry, Nov. 6, 2015, 290(45):27297-310.
Johnston et al., "Isolation of mononuclear cells from tonsillar tissue," Current protocols in immunology, Aug. 2009, 86(1):7.8, 4 pages.
Mousseau et al., "The Tat inhibitor didehydro-cortistatin A prevents HIV-1 reactivation from latency," Mbio, Sep. 1, 2015, 6(4).
PCT International Preliminary Report on Patentability in International Appln. No. PCT/US2017/44494 dated Jan. 29, 2019, 6 pages.
Settleman et al., "Cancer: bet on drug resistance," Nature, Jan. 2016, 529(7586):289-90.
Zhu et al., "Reactivation of latent HIV-1 by inhibition of BRD4," Cell Reports, Oct. 25, 2012, 2(4):807-16.
PCT Written Opinion of the International Search Authority and PCT Search Report for PCT/US2017/44494 dated Sep. 21, 7 pages.
Mckeown et al., "Biased Multicomponent Reactions to Develop Novel Bromodomain Inhibitors", J. Med. Chem 2014, vol. 57, pp. 9019-9027, entire document, especially: p. 9023, Table 2, component 20; p. 9023, Table 3, compound 45.

\* cited by examiner

*Primary Examiner* — Brian J Davis
(74) *Attorney, Agent, or Firm* — Fish & Richardson P.C.

(57) ABSTRACT

The present disclosure provides compounds of Formula (I) and pharmaceutically acceptable salts thereof. Related pharmaceutical compositions are disclosed. Methods of treatment with the disclosed compounds and compositions are also disclosed. Related kits are further disclosed.

20 Claims, 11 Drawing Sheets

A

| Compounds | Binding Energy (Kcal/mol) | |
| --- | --- | --- |
| | PBTOT | GBTOT |
| UMB-32 | -26.67 | -27.67 |
| UMB-58* | -26.35 | -27.40 |
| UMB-59* | -25.62 | -26.80 |
| UMB-136* | -29.48 | -31.60 |
| JQ1 | -10.54 | -15.16 |

* Pose from UMB-32 complex

Figure 2C

SMALL MOLECULE INHIBITORS FOR TRANSCRIPTION FACTORS

CROSS-REFERENCE TO RELATED APPLICATIONS

This application is a National Phase application under 35 U.S.C. § 371 of PCT International Application number PCT/US2017/044494, filed Jul. 28, 2017 which claims priority under 35 U.S.C. § 119(e) to U.S. Provisional Patent Application Ser. No. 62/368,733 as filed on Jul. 29, 2016, the entire disclosures of which are hereby incorporated herein by reference in their entirety for all purposes.

GOVERNMENT SUPPORT

This invention was made with U.S. government support under grants (R01)-DE025447 and R21/R33-AI116180 as awarded by the National Institutes of Health. The U.S. government has certain rights in the invention.

FIELD OF THE TECHNOLOGY

Aspects relate generally to approaches for addressing the human immunodeficiency virus (HIV).

BACKGROUND

HIV is a lentivirus that causes HIV infection and acquired immunodeficiency syndrome (AIDS). Various HIV subtypes are generally associated with resulting immune system failure which allows opportunistic infections and cancers to thrive in a subject.

SUMMARY

In accordance with one or more aspects, a compound of Formula (I) is disclosed. Formula (I):

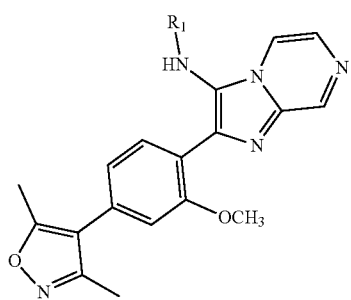

In some aspects, $R_1$ may be cycloalkyl, heterocycloalkyl or alkyl, preferably $R_1$ may be $(C_3-C_{12})$ cycloalkyl or 4- to 12-membered heterocycloalkyl, or $(C_1-C_7)$ alkyl, or a pharmaceutically acceptable salt thereof. In at least some aspects, $R_1$ may be $(C_3-C_{12})$ cycloalkyl or 4- to 12-membered heterocycloalkyl, or $(C_1-C_7)$ alkyl.

In some aspects, the compound may be represented by one of the following structures:

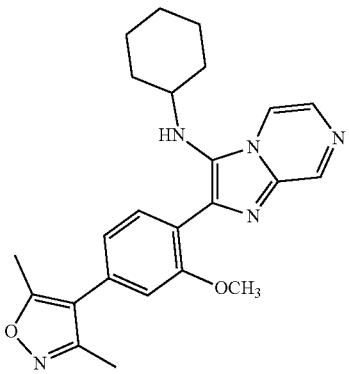
UMB136

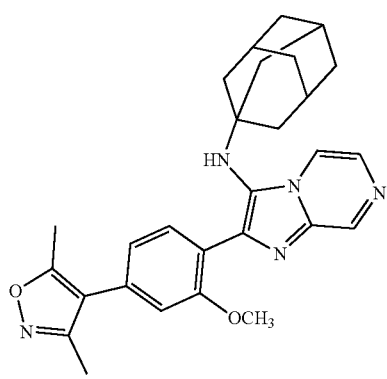
UMB283

In some aspects, the compound may be useful in treating a disease associated with a bromodomain-containing protein in a subject. For example, the compound may be useful in treating HIV-1 or reactivating HIV latency in a subject.

In accordance with one or more aspects, a pharmaceutical composition is disclosed. The composition may comprise a compound as disclosed herein, or a pharmaceutically acceptable salt thereof, and optionally a pharmaceutically acceptable excipient.

In some aspects, the pharmaceutical composition may further comprise a second therapeutic agent. The pharmaceutical composition may be useful in treating a disease associated with a bromodomain-containing protein in a subject. The pharmaceutical composition may, for example, be useful in treating HIV-1 in a subject.

In some aspects, the compound may be a bromodomain and extra-terminal bromodomain inhibitor (BETi). The pharmaceutical composition may comprise a therapeutically effective amount of the compound or pharmaceutically acceptable salt thereof. The pharmaceutical composition may be formulated for oral administration to a subject. In at least some aspects, the composition may be packaged for single use.

In accordance with one or more aspects, a method of treating a disease associated with a bromodomain-containing protein in a subject in need thereof is disclosed. The method may comprise administering to the subject a therapeutically effective amount of a compound as described herein, or a pharmaceutically acceptable salt thereof.

In accordance with one or more aspects, a method of reactivating HIV latency in a subject is disclosed. The method may comprise administering to the subject a therapeutically effective amount of a compound as described herein, or a pharmaceutically acceptable salt thereof.

In accordance with one or more aspects, a method of inhibiting activity of a bromodomain-containing protein in a subject is disclosed. The method may comprise administering to the subject a compound as described herein, or a pharmaceutically acceptable salt thereof, or a pharmaceutical composition as described herein.

In at least some aspects, any of the methods described herein may relate to the HIV-1 disease. An amount and/or a frequency of administration may be sufficient to treat HIV-1. An amount and/or a frequency of administration may be sufficient to reactivate HIV latency in the subject. In at least some aspects, the subject may be human.

In some aspects, the compound or composition may be administered as part of a combination therapy. The compound or composition may be administered in combination with at least one Protein Kinase C (PKC) agonist to reactivate latent HIV-1. The compound or composition may be administered as an analgesic. The compound or composition may be administered as a prophylactic. In at least some aspects, the compound or composition may be self-administered. The compound or composition may be administered in response to a symptom, trigger, or warning sign of HIV-1.

In accordance with one or more aspects, a kit is disclosed. The kit may comprise a compound as described herein, or a pharmaceutically acceptable salt thereof, or a pharmaceutical composition as described herein. The kit may further comprise instructions for using the compound or pharmaceutical composition for the treatment of a subject.

In some aspects, the kit may be useful for treating a disease. The kit may contain a therapeutically effective amount of the compound, salt thereof, or the pharmaceutical composition. The disease may be associated with a bromodomain-containing protein. In at least some aspects, the disease may be HIV-1.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. For purposes of clarity, not every component may be labeled. In the drawings:

FIG. 2C shows binding energies of UMB-32 analogs with BRD4 BD1.

DETAILED DESCRIPTION

Figure 1:
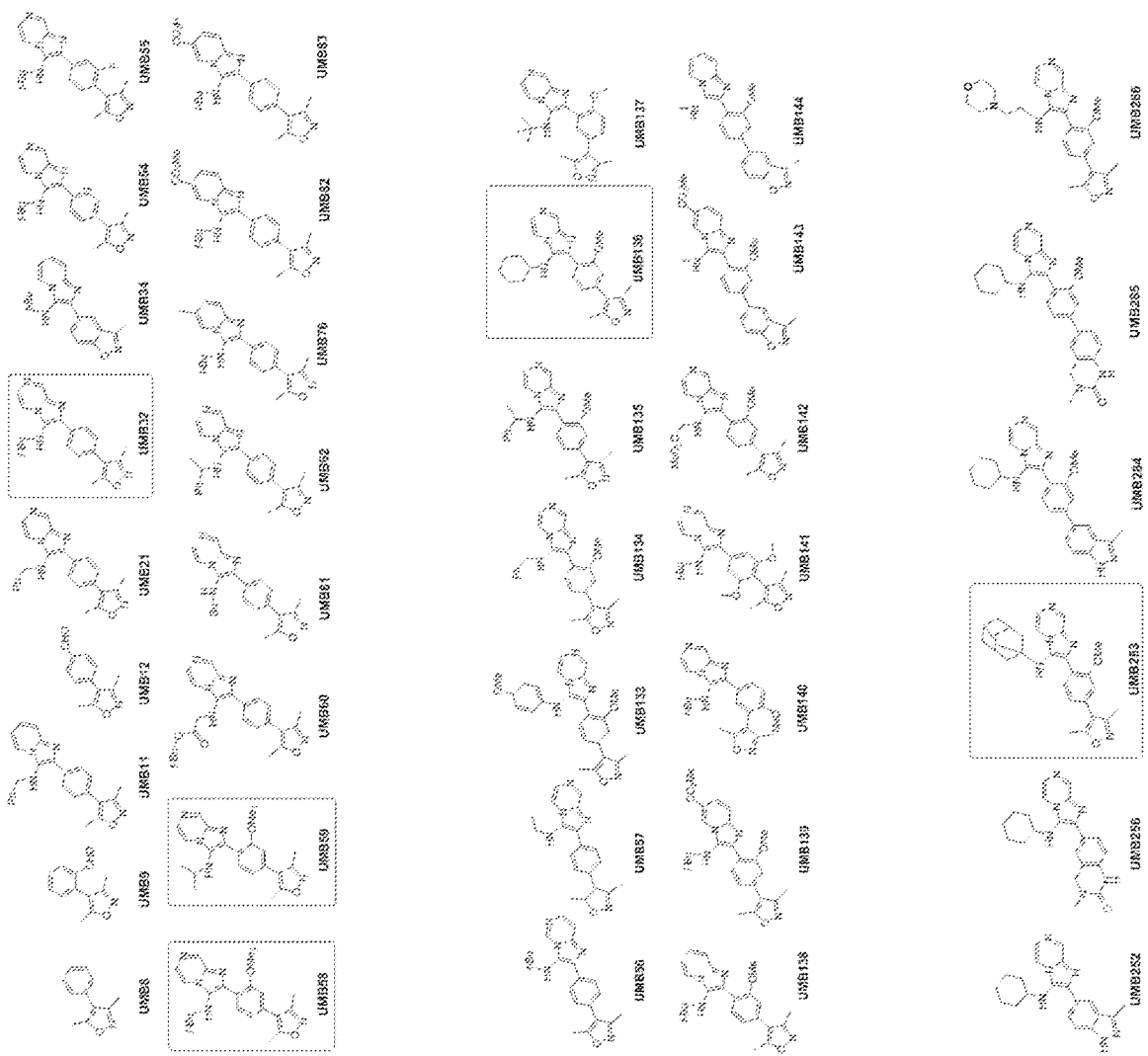
FIG. 1A shows chemical structures of 37 UMB-32 analog compounds.
FIG. 1B shows HIV-1 latency-reversing potential of UMB-58, UMB-59, UMB-136, and UMB-32 using J-Lat A2 cells.

In accordance with one or more embodiments, bromodomain-containing proteins, i.e., the bromo and extra terminal protein (BET) family, may be of substantial biological interest, for example, as components of transcription factor complexes and determinants of epigenetic memory. Without wishing to be bound to any particular theory, some viruses may make sue of BET proteins as part of the process of viral replication.

In accordance with one or more embodiments, small-molecules, e.g., with fragments of 3,5-dimethylisoxazole, are disclosed which may be identified as, e.g., acetyl-lysine mimetics for bromodomain inhibition. In some non-limiting embodiments, compounds UMB136 and/or UMB283 as disclosed herein may provide therapeutically effective biological activity on reactivation of latent HIV-1.

In accordance with one or more embodiments, potent bromodomain inhibitors may reactivate latent HIV-1 for HIV eradication and/or cure therapy.

In accordance with one or more embodiments, bromodomain and extra-terminal bromodomain inhibitors (BETis) that reverse HIV-1 latency are disclosed. BETis have recently emerged as a class of compounds that are promising for HIV-1 latency-reversing purposes.

In accordance with one or more embodiments, the disclosed compounds, compositions, preparation, and/or formulations (terms potentially used interchangeably herein), e.g., UMB136 and/or UMB283, may have potent bioactivity on reactivating latent HIV-1, as well as combined inhibition of BRD4 protein and Protein Kinase C (PKC) as a potential epigenetics-based therapy. Beneficially, the disclosed compounds are much easier to synthesize compared to known compounds for the same purpose.

In accordance with one or more embodiments, a combination of BETis and/or PKC agonists, e.g., bryostatin and/or ingenol, may efficiently reactivate latent HIV-1.

In accordance with one or more embodiments, the disclosed BETis have been developed and characterized for the reversal of HIV-1 latency. AIDS is still currently incurable due to the presence of HIV-1 latent reservoirs, although combination anti-retroviral therapy (cART) efficiently reduces the plasma HIV-1 level to below the detection limit (<50 copies/ml). HIV-1 may remain latent with the presence of cART, impeding the cure of AIDS. A "shock and kill"

approach is considered to be one of the promising strategies to eradicate residual HIV-1, by using small-molecule compounds as latency-reversing agents (LRAs). The development of LRAs to purge latent HIV-1 provides an intriguing strategy for eradication of residual, latent viral reservoirs. Multiple types of LRAs, including BETis, are currently under active development, aiming to reactivate all latent HIV-1 proviruses. For example, without wishing to be bound by any particular theory, antagonism of HIV-1 competitive factor bromodomain containing 4 (BRD4) using bromodomain and extra-terminal domain inhibitor (BETi) JQ1 may facilitate the reversal of HIV-1 latency. In various embodiments, BETis may be actively pursued for HIV-1 eradication therapy. In at least some embodiments, BETis may serve as a class of compounds that are promising for HIV-1 latency-reversing purposes, and may prove to be very promising LRAs by multiple HIV groups.

Without wishing to be bound to any particular theory, HIV-1 depends on many host factors for propagation. Other host factors, however, antagonize HIV-1 and may have profound effects on viral activation. BRD4, as a bromodomain protein that binds to acetylated histones and recruits transcription elongation factor b (PTEF-b), can be a negative regulator of HIV-1 replication. In accordance with one or more embodiments, antagonism of BRD4 with a bromodomain inhibitor can increase proviral transcriptional elongation and alleviate HIV-1 latency in cell-line models. Bromodomain inhibitors may be used in combination with the NF-kB activators Prostratin or PHA to enhance the in vitro reactivation of latent HIV-1 in primary T cells. In accordance with one or more embodiments, the development of novel and potent bromodomain inhibitors can provide insight into the study of reactivation of latent HIV-1, in addition to holding great potential as future therapeutic agents.

Antagonism of HIV-1 competitive factor bromodomain containing 4 (BRD4) using bromodomain and extra-terminal domain inhibitor (BETi) JQ1 may facilitate the reversal of HIV-1 latency. Earlier studies showed that JQ1, the first BETi, is able to reverse HIV-1 latency (Zhu et al., Cell Reports, 2012). Later studies of LRA combinations further demonstrated that (1) JQ1 is the strongest one among the tested first-generation BETis (JQ1, I-BET, I-BET151) and (2) use of JQ1 together with PKC agonists (bryostatin, ingenol) is one of the most potent LRA combinations that reverse HIV-1 latency to the level identical with the use of positive control stimulation, the anti-CD3/CD28 antibodies (Darcis et al., PLoS Pathogen, 2015).

In accordance with one or more embodiments, several issues urge the development of new BETis over JQ1 to be used as LRAs. JQ1 alone is inefficient to reverse HIV-1 latency in primary CD4+ T cells or CD8-depleted PBMCs isolated from cART-treated HIV-1 aviremic patients. Recent studies have also demonstrated that the use of JQ1 as a therapeutic reagent induces the primary and/or acquired drug resistance, at least in the case of anti-cancer treatment (Settleman et al., Nature, 2016). Therefore, it is necessary to develop BETis with more structural diversities to overcome these issues. Using fluorous-tagged multicomponent reactions, a BETi, UMB-32, was developed possessing a different chemical structure from JQ1. UMB-32 strongly binds to bromodomain-containing proteins (BRD4 and TAF1) and potently inhibits the target binding of BRD4 (McKeown et al., J Med Chem, 2014).

UMB-32, along with a related class of inhibitors of transcription factors and uses thereof, is disclosed, for example, in International (PCT) Patent Application Publication No. WO2015/013635 (U.S. Patent Application Publication No. 2016/0168154) to Marineau et al. which is hereby incorporated herein by reference in its entirety for all purposes.

In accordance with one or more embodiments, a facile synthetic strategy and an established biochemical platform were implemented to generate and screen a small set of UMB-32 analogs (37 total) for their HIV-1 latency-reversing potency. UMB-136 was identified as a lead candidate for follow-up studies as described herein. Specifically, it was demonstrated that UMB-136 is able to significantly reverse latent HIV-1 in J-Lat and monocytic cell clones. Consistently, UMB-136 enables the reactivation of latent HIV-1 in an in vitro primary CD4+ T cell model using cells isolated from peripheral blood or lymph node (tonsil). Furthermore, combination of UMB-136 with PKC agonists (prostratin, bryostatin) resulted in a significant response to reactivate latent HIV-1 from the bona fide reservoir cells, the CD8-depleted PBMCs isolated from multiple cART-treated HIV-1 aviremic patients. In all of the above cases, UMB-136 exerts a much better effect than JQ1.

In accordance with one or more embodiments, a synthetic approach for UMB-32/UMB-136 analogs may facilitate future QSAR studies of UMB-136 to optimize its biochemical characteristics so that the HIV-1 latency-reversing effect of UMB-136 will be further enhanced. In accordance with one or more embodiments, an alternative, cell-based approach to quickly screen small-molecule compounds for their HIV-1 latency-reversing effect equivalent to their BETi potency may be useful to identify lead compounds of BETis for HIV-1 eradication therapy and other applications.

The term "bromodomain" refers to a protein domain that recognizes acetylated lysine residues such as those on the N-terminal tails of histones. In certain embodiments, a bromodomain of a BET protein comprises about 110 amino acids and shares a conserved fold comprising a left-handed bundle of four alpha helices linked by diverse loop regions that interact with chromatin. The term "bromodomain-containing protein" or "bromodomain protein" refers to a protein, whether wild-type or mutant, natural or synthetic, truncated or complete, or a variant thereof, that possesses the minimum amino acid sequence sufficient for a functional bromodomain capable of mediating molecular recognition of acetyl-lysine of acetylated lysine residues on the tails of histones. Bromodomain-containing proteins include, for example, fusion proteins comprising a bromodomain and an additional portion having desired functionality (e.g., a reporter portion).

In accordance with one or more embodiments, the present invention provides a compound of Formula (I):

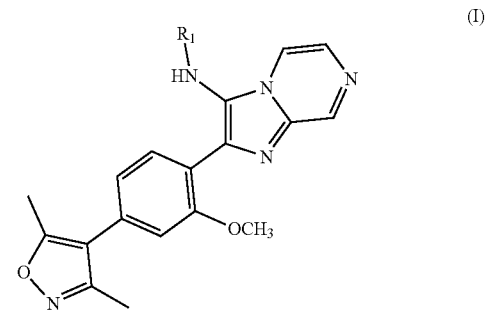

wherein R₁ is cycloalkyl, heterocycloalkyl or alkyl. Preferably, in some non-limiting embodiments, R₁ is (C₃-C₁₂) cycloalkyl or 4- to 12-membered heterocycloalkyl, or (C₁-C₇) alkyl.

Various functional groups and chemical terms used herein are commonly known to those of ordinary skill in the relevant art. Compounds described herein can exist in various isometric forms, e.g., enantiomers and/or diastereomers. Individual isomers and/or mixtures of various isomers are encompassed herein.

In accordance with one or more embodiments, the present invention may provide a compound represented by one of the following structures:

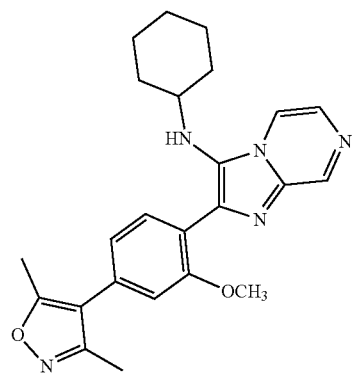

UMB136

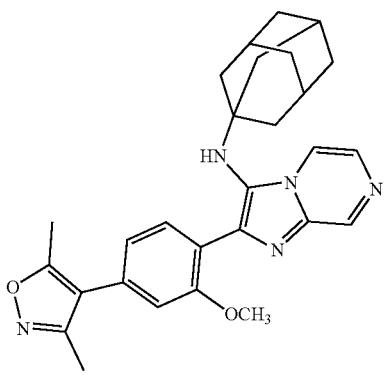

UMB283

In accordance with one or more non-limiting embodiments for illustrative purposes only, an "alkyl" functional group may contain carbon and hydrogen atoms. The atoms may generally be arranged in a chain. The term "alkyl" may include straight, branched and cyclic alkyl groups. The term "alkyl" may encompass both substituted and unsubstituted groups. In certain embodiments, "lower alkyl" may be used to indicate those alkyl groups (cyclic, acyclic, substituted, unsubstituted, branched or unbranched) having 1-6 carbon atoms. In some embodiments, the alkyl group employed may contain 1-20 aliphatic carbon atoms. In certain other embodiments, the alkyl group may contain 1-10 aliphatic carbon atoms. In yet other embodiments, the alkyl group may contain 1-8 aliphatic carbon atoms. In still other embodiments, the alkyl group may contain 1-6 aliphatic carbon atoms. In yet other embodiments, the alkyl group employed may contain 1-4 carbon atoms.

In accordance with one or more non-limiting embodiments for illustrative purposes only, "cycloalkyl" may be a monocyclic, saturated carbocyclyl group having from 3 to 10 ring carbon atoms ("C₃₋₁₀ cycloalkyl"). In some embodiments, a cycloalkyl group may have 3 to 8 ring carbon atoms ("C₃₋₈ cycloalkyl"). In some embodiments, a cycloalkyl group may have 3 to 6 ring carbon atoms ("C₃₋₆ cycloalkyl"). In some embodiments, a cycloalkyl group may have 5 to 6 ring carbon atoms ("C₅₋₆ cycloalkyl"). In some embodiments, a cycloalkyl group may have 5 to 10 ring carbon atoms ("C₅₋₁₀ cycloalkyl"). Unless otherwise specified, each instance of a cycloalkyl group may be independently unsubstituted (an "unsubstituted cycloalkyl") or substituted (a "substituted cycloalkyl") with one or more substituents.

In accordance with one or more non-limiting embodiments for illustrative purposes only, the term "heterocycloalkyl" may relate to a non-aromatic monocyclic or polycyclic ring comprising carbon and hydrogen atoms and at least one heteroatom, preferably, 1 to 4 heteroatoms selected from nitrogen, oxygen, and sulfur. Non-limiting examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted, e.g., with one or two suitable substituents. The heterocycloalkyl group may be a monocyclic or bicyclic ring.

In accordance with one or more non-limiting embodiments for illustrative purposes only, "heterocyclyl" or "heterocyclic", may refer to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. "Heterocyclyl" may also include ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl may be independently optionally substituted, i.e., unsubstituted (an "unsubstituted heterocyclyl") or substituted (a "substituted heterocyclyl") with one or more substituents.

Pharmaceutically acceptable salts, solvates, hydrates, polymorphs, co-crystals, tautomers, stereoisomers, isotopically labeled derivatives, and/or prodrugs of the compound of Formula (I), e.g., but not limited to UMB136 and UMB283, are also disclosed. In at least some embodiments, a compound of Formula (I) and pharmaceutically acceptable salts thereof are provided.

In accordance with one or more embodiments, compounds may be inhibitors of bromodomain-containing proteins. In certain embodiments, the compounds may bind to a bromodomain-containing protein. Disclosed compounds may exhibit a greater binding affinity to bromodomain-containing proteins than may be demonstrated to one or more other proteins. In at least some embodiments, extra-terminal bromodomain inhibitors (BETis) are disclosed.

In accordance with one or more embodiments, disclosed compounds may be useful in the treatment of a disease associated with activity of a bromodomain-containing protein such as but not limited to those disclosed herein. In at least some embodiments, the activity of a bromodomain-containing protein, such as may be reflected by a half maximal inhibitory concentration ($IC_{50}$) value, may be inhibited, e.g., selectively or non-selectively, by the disclosed compounds. It is known in the art that a bromodomain-containing protein is implicated in a wide range of diseases. useful in treating HIV-1 or reactivating HIV latency in a subject. In at least some embodiments, disclosed compounds may be useful in treating HIV-1 and/or reactivating HIV latency in a subject.

In accordance with one or more embodiments, pharmaceutical or therapeutic compositions comprising a disclosed compound, e.g., a compound of Formula (I), e.g., UMB136 and UMB283, or a pharmaceutically acceptable salt, solvate, hydrate, polymorph, co-crystal, tautomer, stereoisomer, isotopically labeled derivative, or prodrug thereof, and optionally a pharmaceutically acceptable excipient, are provided. In at least some embodiments, a pharmaceutical composition comprises a compound of Formula (I), or a pharmaceutically acceptable salt thereof, and optionally a pharmaceutically acceptable excipient is disclosed. In at least some embodiments, a pharmaceutical composition includes a pharmaceutically acceptable excipient.

In accordance with one or more embodiments, a compound is provided in an effective amount in a pharmaceutical composition. The effective amount may be a therapeutically effective amount or a prophylactically effective amount. The effective amount may be an amount effective for treating and/or preventing a disease, such as but not limited to those described herein, e.g., HIV, e.g., HIV-1. In at least some embodiments, the disease may be associated with a bromodomain-containing protein. The effective amount may be an amount effective for inhibiting the activity of a bromodomain-containing protein, e.g., in a subject or a cell. The binding of a bromodomain of a bromodomain-containing protein to an acetyl-lysine residue may be inhibited. Various inhibitions exhibited may be by at least about 1%, 5%, 10%, 20%, 30%, 40%, 50%, 60%, 70%, 80%, or 90%. In some embodiments, an effective amount may modulate the expression of a gene that is regulated by a bromodomain-containing protein.

In accordance with one or more embodiments, treatment of a disease or condition refers to reducing the severity or frequency of at least one symptom of that disease or condition, compared to a similar but untreated patient. Treatment can also refer to halting, slowing, or reversing the progression of a disease or condition, compared to a similar but untreated patient. Treatment may comprise addressing the root cause of the disease and/or one or more symptoms.

In accordance with one or more embodiments, a therapeutically effective amount refers to a dose sufficient to prevent advancement, or to cause regression of a disease or condition, or which is capable of relieving a symptom of a disease or condition, or which is capable of achieving a desired result.

In some non-limiting embodiments, an effective amount of a compound may vary from about 0.001 mg/kg to about 1000 mg kg in one or more dose administrations for one or several days (depending on the mode of administration). In certain embodiments, the effective amount per dose varies from about 0.001 mg kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In accordance with one or more embodiments, pharmaceutical compositions described herein may be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit. Unit doses relate to a predetermined amount of active ingredient. The does may be administered to a subject and/or a convenient fraction thereof.

In accordance with one or more embodiments, pharmaceutically acceptable excipients used in the manufacture of disclosed pharmaceutical compositions may include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition. Examples of excipients in these various categories are widely known to those of ordinary skill in the relevant art.

Various modes of administration for the pharmaceutical or therapeutic compositions are disclosed herein as commonly known to those of skill in the art.

In some embodiments, a dosage form may be a liquid dosage form for oral or parenteral administration These may include pharmaceutically acceptable emulsions, microemulsions, solutions, suspensions, syrups and elixirs. Inert diluents and/or adjuvants, and or solubilizing agents may commonly be incorporated. Likewise, solid dosage forms for oral administration may include capsules, tablets, pills, powders, or granules. These may include pharmaceutically acceptable excipients, carriers, fillers, binders, humectants, disintegrating agents, retardants, absorption accelerators, and/or lubricants. The active ingredient may be microencapsulated.

In some embodiments, a therapeutic preparation may be injectable, e.g. intradermal. In other embodiments, a therapeutic preparation may be formulated for rectal or vaginal administration. Related devices, such as suppository or syringe, for delivery of the therapeutic preparation are disclosed herein. Topical and/or transdermal administration, e.g., those involving ointments, gels, sprays, and patches, are also disclosed. Likewise, pulmonary (coarse powder), intranasal, or ophthalmic delivery may be implemented.

In accordance with one or more embodiments, the compositions may be administered to a subject for treatment of a disease or a condition. In at least some embodiments, the subject may be human. In other embodiments, the subject may be another type of mammal. The preparations may generally be administrable to animals of all types, e.g., domesticated animals, companion animals, livestock, or research animal. Modification of formulations for various subjects is commonly known in the relevant art. The subject may be in need of treatment of a target indication, disease, or condition as described herein. A subject may be diagnosed with a target indication or disease, e.g., HIV, e.g., HIV-1. A subject may be selected for treatment on that basis.

In accordance with one or more embodiments, a disease, e.g., HIV, may be treated at various stages. For example, the stages of HIV infection include acute/primary infection, latency, and AIDS. A compound or composition disclosed herein may be administered in response to, or in order to prevent a symptom of a disease or disorder. In accordance with one or more embodiments, HIV, e.g., HIV-1, may be associated with signs and symptoms including but not limited to: fever, swelling, inflammation, rash, muscle pain, weight loss, cough, malaise, sores, infection, low CD4+ T cell count (i.e. fewer than 200 per microliter), cancer, and other conditions. HIV infection may also manifest in various pulmonary, gastrointestinal, neurological, and psychiatric conditions. In at least some embodiments, the pharmaceutical or therapeutic compositions disclosed may be useful in treating HIV-1 or reactivating HIV latency in a subject.

Dosage, e.g., total daily dosage, may be decided by an attending physician and may vary based on age, gender, race, diet, health, weight, etc. of a subject. The subject may be male or female. The subject may be of an age less than 1, or between 1-5, 5-10, 10-20, 20-30, 30-40, 40-50, 50-60, or over 60 years. Mode of administration, disease progression, risk, course of treatment, combination therapies, etc. may also impact dosage. A unit dosage may be administered daily, multiple times a day, multiple times a week, or multiple times a month. Course of treatment may, for example, span a day, multiple days, multiple weeks, or multiple months.

Purely for illustrative purposes, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form. In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

Various combination therapies are disclosed. Compounds or compositions described herein may be administered in combination with one or more additional pharmaceutical agents. The additional pharmaceutical agent may exhibit synergy with the disclosed compounds and compositions. The additional pharmaceutical agent may be administered concurrently with the disclosed compounds and compositions, or instead for a period of time prior to or subsequent their administration. The additional pharmaceutical agent may improve the activity of the disclosed compounds and compositions. The additional pharmaceutical agent may independently exhibit efficacy for a target indication, disease, or condition. Alternatively, the additional pharmaceutical agent may be associated with a different desired effect. The additional pharmaceutical agent may include small molecules such as a drug compound approved for use in connection with a target indication. Other non-limiting pharmaceutical agents may also comprise peptides, proteins, nucleic acids, hormones, lipids, and vitamins. In some embodiments, a subject may already have a therapeutically effective level of an additional pharmaceutical agent at the time of administration of the present compounds and compositions. An additional therapeutic agent may or may not be an inhibitor of a bromodomain-containing protein.

In accordance with one or more embodiments specific to the treatment of HIV or reactivating HIV latency in a subject, combination therapies may include a second therapy such as, but not limited to an antiretroviral (ARV) therapy. An ARV therapy may involve one or more relevant drug classes which include nucleoside reverse transcriptase inhibitors (NRTIs), non-nucleoside reverse transcriptase inhibitors (NNRTIs), protease inhibitors (PIs), fusion and entry inhibitors, pharmacokinetic enhancers, and integrase strand transfer inhibitors (INSTIs). In at least some embodiments, a second therapy may be an alternative medical approach, e.g., homeopathic medicine, or involve a form of physical therapy. The disclosed compounds and methods may be used in conjunction with an HIV vaccine. In some specific embodiments, disclosed compounds and compositions may be administered in combination with at least one Protein Kinase C (PKC) agonist to reactivate latent HIV-1.

In accordance with one or more embodiments, a kit may comprise a compound or composition as disclosed herein. The kit may be useful for treating a disease or condition as described herein, e.g., HIV or HIV-1. A kit may be useful for inhibiting binding of a bromodomain of a bromodomain-containing protein. The kit may include instructions for administering the compound or pharmaceutical composition. Regulatory information may be included in the kit. The kit may include instructions for treating and/or preventing a disease or condition as described herein, e.g., HIV or HIV-1.

In accordance with one or more embodiments, methods of using the disclosed compounds and compositions for treatment of a disease or condition are disclosed. The disease may be associated with a bromodomain-containing protein, e.g., associated with the activity of the protein or the function of a bromodomain of the protein. The disease may be a proliferative disease in some non-limiting embodiments. Other methods may relate to inhibiting activity, e.g., binding, e.g., selectively inhibiting, of a bromodomain-containing protein, e.g., BRD4. Activity may, for example, be inhibited by at least about 1%, 5%, 10%, 20%, 30%, 40%, 50%, 60%, 70%, 80%, or 90%. Still other methods may relate to modulating gene expression otherwise regulated by a bromodomain-containing protein. The various methods may relate to in vitro, ex vivo, or in vivo cell work.

In accordance with one or more embodiments, a method may comprise administering to a subject, e.g., a subject in need thereof, an effective amount of a compound or composition as disclosed herein. The effective amount may be a therapeutically effective amount as described herein. The disease or condition may thereby be treated by the disclosed methods.

In accordance with one or more embodiments, the disclosed BETis may find particular utility in terms of treating HIV, e.g. HIV-1 as disclosed herein. In this regard, specific methods of treating HIV or HIV-1 are disclosed which may involve administering an effective amount of a compound or composition as described herein to a subject, thereby treating HIV in the subject.

In accordance with one or more embodiments, a method of reactivating HIV latency in a subject may comprise administering to the subject a therapeutically effective amount of a compound as described herein, or a pharmaceutically acceptable salt thereof.

In some embodiments, the disclosed BETis may also find utility as an important class of compounds with multiple applications for treatment of malignancy, inflammation, and viral infection. For example, non-limiting embodiments may be useful for the treatment of various infections, e.g., other viruses beyond HIV-1, various forms of cancer, inflammatory diseases, and/or autoimmune diseases.

One or more other embodiments may relate to methods of screening a library of compounds, and pharmaceutical acceptable salts thereof, to identify a compound, or a pharmaceutical acceptable salt thereof, that is useful in the present methods, e.g., methods of treatment, e.g., treating HIV. In certain embodiments, the library of compounds is a library that includes the compounds disclosed herein. In certain embodiments, the methods of screening a library include obtaining at least two different compounds, and performing at least one assay using the different compounds. In certain embodiments, at least one assay is useful in identifying a compound that is useful in the inventive methods. In certain embodiments, the assay is performed to detect one or more characteristics associated with the treatment and/or prevention of a disease described herein, or with the inhibition of activity, e.g., of a bromodomain-containing protein as described herein. Various assays are known to those of ordinary skill in the relevant art.

In at least some embodiments, UMB136 and/or UMB283 have potent bioactivity on reactivating the latent HIV-1 and combined inhibition of BRD4 protein and Protein Kinase C (PKC) as a potential epigenetics-based therapy. They are also much easier to synthesize compared to the known compounds. In accordance with one or more embodiments, the combination of BETis and PKC agonists (bryostatin, ingenol) can efficiently reactivate latent HIV-1. In accordance with one or more embodiments, potent small-molecules with fragments of 3,5-dimethylisoxazole have been identified as acetyl-lysine mimetics for bromodomain inhibition. In accordance with one or more embodiments, the disclosed compounds may be used clinically for HIV eradication and cure therapy.

The function and advantages of these and other embodiments will be more fully understood from the following non-limiting example. The example is intended to be illustrative in nature and is not to be considered as limiting the scope of the embodiments discussed herein.

EXAMPLE

The potency of bromodomain and extra-terminal domain inhibitors (BETi) as potential new latency reversing agents (LRA) was evaluated. Using fluorous-tagged multicomponent reactions, second-generation 3,5-dimethylisoxazole BETis based on an imidazo[1,2-a] pyrazine scaffold were developed. The lead compound using the imidazo [1,2-a] pyrazine scaffold 32 (UMB-32) demonstrated a strong binding affinity with bromodomain-containing proteins (BRD4 and TAF1) as well as a potent inhibitory effect on BRD4. Thirty seven UMB-32 derivatives were screened and one, UMB-136, was identified to reactivate HIV-1 in multiple cell models of HIV-1 latency with better efficiency than either the first-generation methyl-triazolo BETi (JQ1) or UMB-32. UMB-136 was determined to enhance HIV-1 transcription and increase viral production through the release of P-TEFb. UMB-136 was determined to enhance the latency-reversing effects of PKC agonists (prostratin, bryostatin-1) in CD8-depleted PBMCs containing latent viral reservoirs. The results illustrate that structurally improved BETis, such as UMB-136, may be useful as promising LRAs for HIV-1 eradication.

The subjects included combinatory antiretroviral therapy (cART)-treated, HIV-infected, aviremic patients who were recruited by the AIDS clinic at the Strong Memorial Hospital of the University of Rochester Medical Center (Rochester, N.Y.). All study subjects had been treated with cART for >3 years, had an undetectable plasma HIV-RNA level (<50 copies/ml) for at least 6 months, and a normal CD4+ T lymphocyte count (>300 cells/mm3) at the time of the leukapheresis process. The study was approved by the University of Rochester Research Subjects Review Board with an assigned number (#RSRB00053667).

The syntheses of UMB-32 analogs, including UMB-58, -59, -136, and -283, were accomplished as described in McKeown et al. *J Med Chem.* 2014 Nov. 13, 57(21):9019-27 using a two-step synthesis involving a three-component (Groebke-Blackburn-Bienayme) reaction followed by Suzuki coupling.

AMBER 14 software was used to implement molecular mechanics Poisson Boltzmann (MM-PBSA) and related generalized Born (MM-GBSA), which in turn were used to calculate the relative binding affinities of BETis to BRD4 BD1. The calculated energies were further decomposed into insightful interaction components. Cartesian coordinates for protein-ligand complexes were determined by aligning second generation BETis (UMB-58, UMG-59 and UMB-136) with the characterized pose of the parental ligand in a crystal structure of UMB-32, bound to BRD4 BD1. (PDB code: 4WIV). The new complexes were acquired and initially minimized using Chimera-1.10.2. MD simulations in explicit solvent (FF14SB force field, TIP3P solvent model, 50 ps of heating, 50 ps of density equilibration, 500 ps of constant pressure equilibration at 300K, followed by 4 production runs of 500 ps long each) were used to obtain the equilibrium conformations for each protein-ligand complex, free protein, and free ligand. Continuum solvents (PB and GB-OBC) replaced explicit solvent in the relative free energy calculation phase. The entropic contribution was not added as it is assumed not to alter the relative binding affinity.

The CD4+ T-lymphoid cell lines included Jurkat, J-Lat A2 (harboring an LTR-Tat-IRES-GFP construct), J-Lat 6.3, 8.4, 9.2, 10.4 (containing a full-length integrated HIV-1 genome with a defective envelop, that express GFP upon activation). Monocytic THP89GFP cells were provided by David Levy (New York University). Jurkat cells were cultured in RPMI with 10% FBS. THP89GFP and Primary CD4+ helper T cells (Sanguine Biosciences, Sherman Oaks, Calif. and Lonza Group Ltd., Basel, Switzerland) were cultured and maintained respectively in complete medium (RPMI 1640 with 10% FBS, lx glutamine, lx MEM non-essential amino acid solution, and 20 mM HEPES).

Pseudo-typed HIV-1 NL4-3 viruses were produced by using TurboFect (ThermoFisher Scientific, Waltham, Mass.) to co-transfect pCG-VSV-G and HIV-1 NL4-3-Luc (ΔEnv) plasmids into HEK293T cells. Full-length HIV-1 NL4-3 (X4 tropic) viruses were created similarly by transfecting pNL4-3 (X4) plasmid into HEK293T cells.

Methyl-triazolo BETi (JQ1) was purchased from Sigma-Aldrich, St. Louis, Mo. Prostratin, SAHA, and bryostatin-1 were purchased from Santa Cruz Biotechnology, Dallas, Tex. Antibodies against CD3 and CD28 were purchased from eBioscience, San Diego, Calif. TGF-β, IL-12, and IL-4 antibodies were purchased from R&D Systems, Minneapolis, Minn. IL-2 and Nevirapine were obtained from NIH AIDS Reagent Program.

Flow cytometry assays were performed by culturing J-Lat A2 cells in a 48-well plate at 1×105 cells per well in a total volume of 200 µl Roswell Park Memorial Institute (RPMI) media supplied with 10% fetal bovine serum (FBS). Wells were treated with 5 µM of compound or dimethyl sulfoxide (DMSO). GFP-positive cells were acquired and analyzed by flow cytometry at 24 hours post treatment.

The HIV-1 latency-reversing effect of UMB-136 was evaluated on different reservoirs (lymphocytes and macrophages), J-Lat cell clones (6.3, 8.4, 9.2, and 10.4) and THP89GFP were treated with DMSO, JQ1 (1 μM), or UMB-136 (2.5, 5 μM for J-Lat cells, 5 μM for THP89GFP). For the investigation of synergistic effects JLat clones were treated with UMB-136 (2.5 μM), JQ1 (1 μM), SAHA (0.5 μM) or prostratin (1 μM) or DMSO as a control. Drugs were used alone or in combination. Flow cytometry was conducted at 24 hours post treatment and GFP-positive cells were quantified.

All flow cytometry assays were conducted using an Accuri C6 Flow Cytometer (Accuri, Ann Arbor, Mich.). Cell debris and aggregates were excluded by gating on the Forward Scatter (FS) and Side Scatter (SS) parameters.

Pull-down and Immunoprecipitation (IP) assays were performed by incubating HEK293 cell lysate with either biotinylated UMB-136 or biotin in DMSO at 4° C. overnight with orbital rocking. MyOne™ Streptavidin T1 Dynabeads™ (Invitrogen, Carlsbad, Calif.) were added to the mixture which was then incubated for 2 hours. Beads were washed and then boiled to elute precipitated proteins, which were subjected to immunoblotting using BRD4 antibody (Bethyl Laboratories, Inc., Montgomery, Tex.) or BRD2 antibody (Santa Cruz Biotechnology, Dallas, Tex.).

Tat-Flag expressing HeLa cells were treated with UMB-136 (2.5 μM) or DMSO for 24 hours, then incubated with Magnetic Flag Conjugated beads (Clontech, Mountain View, Calif.) at 4° C. for overnight with orbital rocking. Beads were washed and boiled, then immunoblotting was performed using Cyclin T1 antibody (Santa Cruz Biotechnology, Dallas, Tex.).

Cell viability assays were performed by culturing Jurkat cells in a 48-well plate at 1×105 cells per well in a total volume of 250 μl RPMI media with 10% FBS. Compounds (JQ1, UMB-136, or DMSO) were added. After an incubation period of 24 hours, cells were lysed. The total ATP content was measured using Cell Titer Glo (Promega Corporation, Madison, Wis.).

Effects of the LRAs on HIV transcription were determined by quantitative polymerase chain reaction (qPCR) assay. Jurkat cells were transduced with VSV-G pseudotyped HIV-1 NL4-3-Luciferase virus for 8 hours and treated with compounds (UMB-32, UMB-136, JQ1, or prostratin) for 24 hours. Cells were collected and subjected to mRNA extraction (RNeasy® Mini Kit, Qiagen, Hilden, Germany) and reverse transcription (iScript™ cDNA Synthesis Kit, Bio-Rad, Hercules, Calif.). The qPCR assays were conducted using the iTaq™ Universal SYBR® Green Supermix (Bio-Rad, Hercules, Calif.) on the CFX Connect™ Real-Time PCR System (Bio-Rad, Hercules, Calif.). The following qPCR primers were used: Initiation (10-59 bp) (forward, 5'-GTT AGA CCA GAT CTG AGC CT-3'; reverse, 5'-GTG GGT TCC CTA GTT AGC CA-3'); Elongation (29-180 bp) (forward, 5'-TGG GAG CTC TCT GGC TAACT-3'; reverse, 5'-TGC TAG AGA TTT TCC ACA CTG A-3').

To determine the effect of UMB-136 on HIV-1 replication, Jurkat cells were infected with full-length HIV-1 NL4-3 (X4) viruses for 8 hours before being treated with compounds (UMB-136, JQ1, or prostratin) for 24 hours. The medium was collected and subjected to viral RNA extraction, reverse transcription, and qPCR assays by using Lenti-X™ qRT-PCR Titration Kit (Clontech, Mountain View, Calif.) following the manufacturer's instructions.

To acquire primary CD4+ T cells, primary CD4+ T cells were isolated from either lymphoid tissue (tonsil) or from the peripheral blood of two donors. Tonsils were isolated from HIV-negative donors, with obstructive sleep apnea (OSA), whom required surgical removal of their tonsils. Isolation of tonsillar mononuclear cells (TMC) was performed as described in Johnston et al. *Curr Protoc Immunol* Chapter 7, Unit 7-8. In brief, fresh, healthy tonsils kept in ice-cold 1× Hank's Balanced Salt Solution (HBSS) with antibiotics (100 U/mL penicillin, 100 ug/mL streptomycin, 5 ug/mL gentamicin, 0.5 ug/mL amphotericin) were cut into 3- to 10-mm fragments with scalpels then pushed through a 3-inch stainless steel sieve using the flat end of a 5-mL plastic syringe plunger. After breaking up any cell clumps, a 35 mL cell suspension was passed through a sterile 40-μM plastic cell strainer (Fisher Scientific, Hampton, N.H.) and subsequently overlaid on 10-mL Ficoll-Hypaque (GE Healthcare, Little Chalfont, United Kingdom), before being centrifuged at 1000×g for 20 min without braking. Mononuclear cells were collected from the interface and washed three times with ice-cold 1×HBSS then re-suspended in cryopreservative medium for storage in liquid nitrogen. Tonsillar CD4+ T cells were purified using the CD4+ T cell Isolation Kit (Miltenyi Biotec, Cologne, Germany) according to the manufacturer's instructions. Peripheral CD4+ T cells were purchased from Lonza Group Ltd., Basel, Switzerland.

The LRA effect of UMB-136 was studied by modifying slightly a primary CD4+ T cell model of HIV-1 latency as described in Bosque et al. *Methods*. 2011 January 53(1):54-61 and Huang et al. *J Biol Chem* 290, 27297-310. In brief, primary T cells were activated using CD3/CD28 antibodies and then infected with full-length HIV-1 NL4-3 (X4) viruses. Cells were treated with TGF-β, anti-IL12, and anti-IL4 antibodies (R&D Systems, Minneapolis, Minn.) for non-polarization to allow for the establishment of latent HIV-1. These cells were treated with compounds 2.5 UMB-136 or 1 μM JQ1 on day 16 post-infection. 24 hours later the compounds were washed away and cells were re-suspended in fresh complete RPMI media. On day 21, 5 days post treatment, the supernatant was collected for quantification of newly produced viruses using the Lent-X™ qRT-PCR Titration Kit (Clontech, Mountain View, Calif.) following the manufacturer's instructions.

To study CD8-depleted peripheral blood mononuclear cells (PBMC), PBMCs were isolated from fresh whole blood of the cART-treated HIV-infected aviremic study subjects using the Ficoll-Hypaque gradient method, as described in Bouchat et al. *AIDS* 26, 1473-1482. Whole blood was diluted in 1× Phosphate-Buffered Saline (PBS) (without $Ca^{2+}$ or $Mg^{2+}$) at 1:1 ratio. Then, 26 mL of the cell suspension was gently overlaid onto 14 ml of Ficoll-Paque (GE Healthcare, Little Chalfont, United Kingdom) in a 50 mL conical tube. This was centrifuged for 20 min at 966×g without braking, at room temperature. The PBMC band from interface was collected and transferred to a new sterile 50 mL conical tube. PBMCs were washed three times using 1×PBS with 5 mM Ethylenediaminetetraacetic acid (EDTA). Cells were allowed to rest in complete RPMI media in the presence of Nevirapine (600 nM) and IL-2 (30 IU/ml) for 3 days. CD8+ T cells were depleted by negative selection using CD8 MicroBeads (Miltenyi Biotec, Cologne, Germany), following the manufacturer's instructions.

An ultra-sensitive nested qPCR assay was used to quantify reactivated HIV-1 viruses according to the protocol described in Mousseau et al. *MBio* 6, e00465. CD8-depleted PBMCs were cultured at 2×106 cells/ml and stimulated with indicated compound combinations for 48 hours: UMB-136 (2.5 µM), JQ1 (1 µM), prostration (250 nM), bryostatin-1 (10 nM), anti-CD3/CD28 antibodies (1:1), or DMSO. Supernatants were collected and viral RNA extraction was performed using the QIAmp® Viral RNA kit (Qiagen, Hilden, Germany) following the manufacturer's protocol. Extracted viral RNA was subsequently treated with DNase I (Invitrogen, Carlsbad, Calif.) for 10 min at 25° C. then inactivated by EDTA treatment for 10 min at 65° C. A Reverse transcription coupled qPCR assay was carried out using the Superscript® III One-Step RT-PCR System with Platinum® Taq High Fidelity (Life Technologies, Carlsbad, Calif.) in a total volume of 50 µl. Gag gene-specific primers were used for PCR are as follows: forward (Q1), 5'-ATG CCA CGT AAG CGA AAC TCT GGG TCT CTC TGG TTA GAC-3'; reverse (Q2), 5'-CCA TCT CTC TCC TTC TAG C-3'. The following thermal cycles were used: 50° C. for 30 min, 94° C. for 2 min, and 16 cycles of [94° C. for 15 sec, 62° C. for 30 sec, 68° C. for 60 sec], with a final elongation step at 65° C. for 5 min. The pre-amplified RT-PCR products were purified using the QIAquick® PCR Purification Kit (Qiagen, Hilden, Germany) and further subjected to a second nested qPCR assay using the TaqMan® Universal PCR Master Mix (Applied Biosystems, Foster City, Calif.) in the total volume of 25 µl. Primers and probes used for nested PCR are as indicated: forward (Q3), 5'-ATG CCA CGT AAG CGA AAC T-3'; reverse (Q4), 5'-CTG AGG GAT CTC TAG TTA CC-3'; probe, 5'-6FAM/CAC TCA AGG CAA GCT TTA TTG AGG C/6-TAMSp-3'. The thermal cycles included one for UNG incubation (50° C. for 2 min), followed by initial denaturation (95° C., 10 min), 45 cycles of amplification (95° C., 15 sec; 50° C., 20 sec; 60° C., 1 min). All PCR assays were conducted on the CFX Connect™ real time PCR detection system (Bio-Rad, Hercules, Calif.). A serial dilution of HIV-1 IIIB viruses with known concentrations at a series of dilutions were used to create a standard curve for the absolute quantification of reactivated HIV-1 viruses in supernatants.

UMB-136 was Determined to be a Leading UMB-32 Based BETi

Figure 1B:
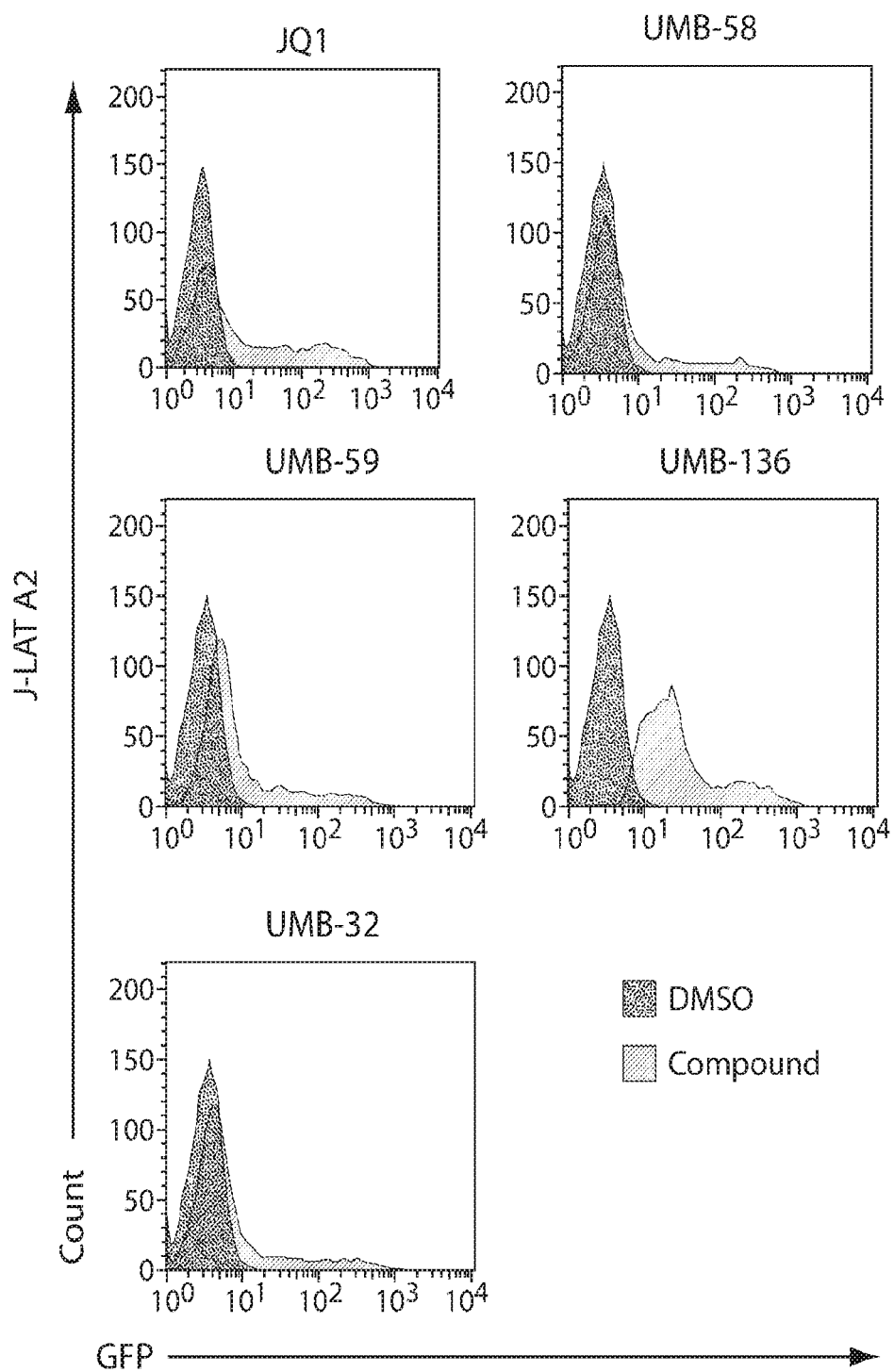

The HIV-1 latency-reversing potential of 37 UMB-32 analogs was determined using J-Lat A2 cells (FIG. 1A). Four compounds (UMB-32, UMB-58, UMB-59, and UMB-136) significantly induced HIV-1 reactivation; with UMB-58, UMB-59, and UMB-136 proving to be more potent than UMB-32 and UMB-136 being the most effective of all (FIG. 1B). While not wishing to be bound by any particular theory, it is postulated that this is due to the presence of an additional methoxy group (R—OCH3), which is shared by the three aforementioned compounds but not with UMB-32 (FIG. 1A). A structural mimic of UMB-136, UMB-283 shows similar potency in reversing HIV-1 latency. Cell viability assays were performed in Jurkat cells. It was determined that 2.5 µM of UMB-136 causes the same viability as 1 µM of JQ1. Thus, these concentrations were used for each drug. The data are summarized in FIG. 1.

Figure 2A:
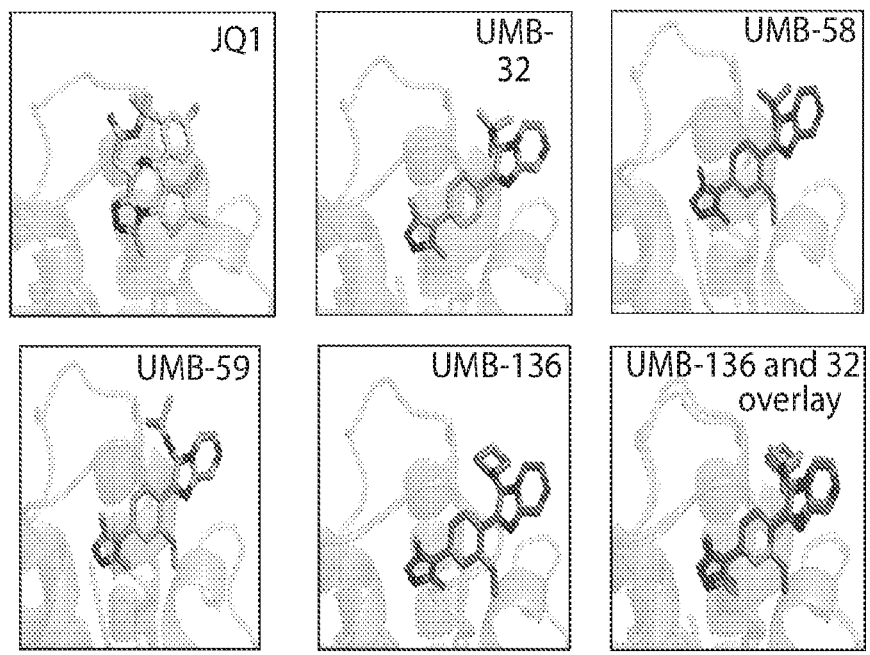
FIG. 2A shows images of binding of UMB-32 analogs with bromodomains (BDs) of BRD4.
Figure 2B:
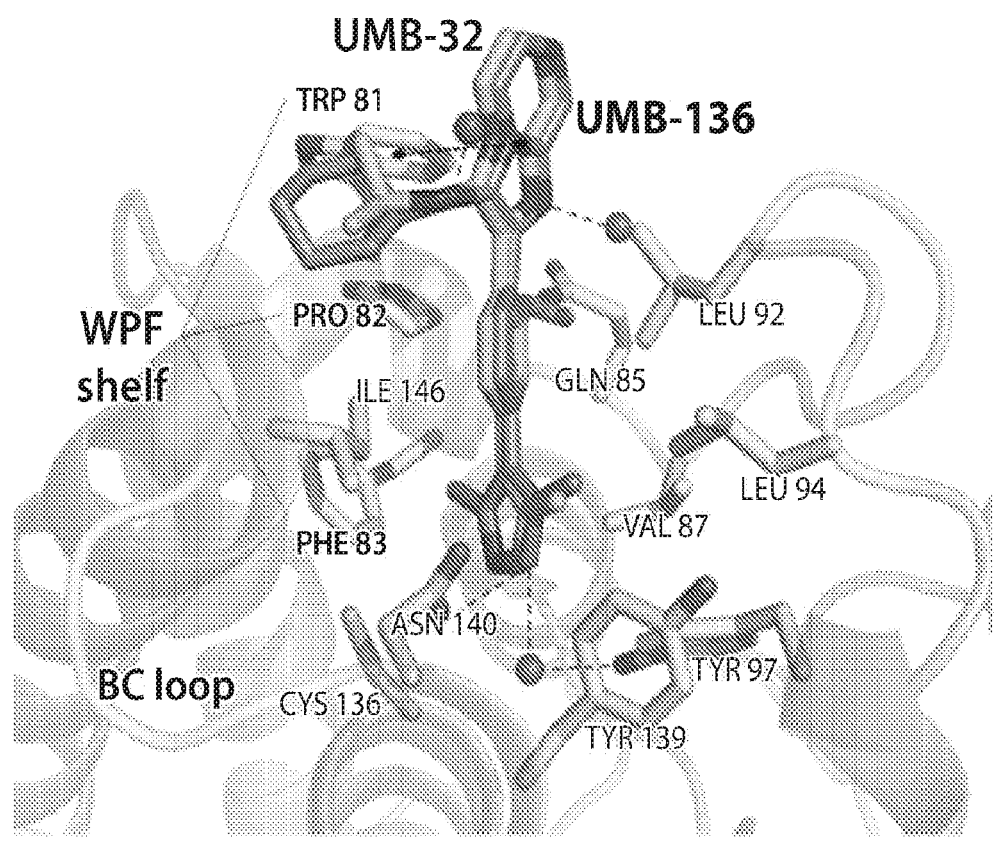
FIG. 2B shows image of binding of UMB-136 with BRD4 BD1, by imposing the compound onto available structure data of UMB-32 bound to BRD4 BD.
Figure 2D:
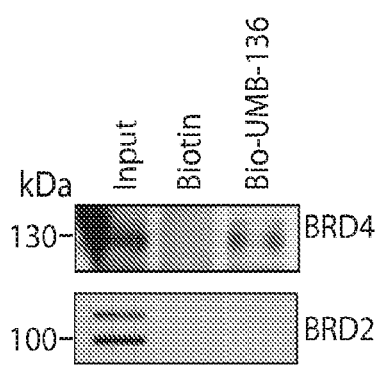
FIG. 2D shows that UMB-136 binds to endogenous BRD4 but not BRD2.
Figure 2E:
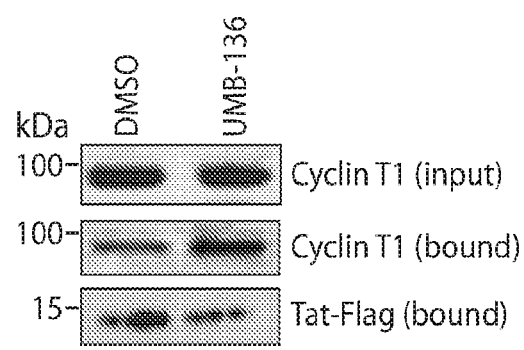
FIG. 2E shows that UMB-136 treatment resulted in greater protein association between P-TEFb (CCNT1) and Tat.

UMB-136 was Determined to Enhance HIV-1 Transcription and Viral Production by Releasing P-TEFb Structurally, out of all UMB-32 derivatives, UMB-136 exclusively contains a cyclohexane group (FIG. 1A). The binding of UMB-32 analogs with bromodomains (BDs) of BRD4 may correlate with their potency to reverse HIV-1 latency. The binding energies of UMB-58, UMB-59, and UMB-136 with BRD4 BD1, were calculated by imposing these compounds onto available structure data of UMB-32 bound to BRD4 BD1 (FIG. 2A, B). Notably, UMB-136 had the lowest binding energy (PBTOT: −29.48 Kcal/mol; GBTOT: −31.60 Kcal/mol) among all UMB-32 analogs and was also lower than that of JQ1 (FIG. 2C). This is consistent with previous HIV-1 latency reversing assay results where UMB-136 was the most effective of compared compounds. In addition to other groups, it has been shown that BRD4 inhibition by JQ1 increases Tat-dependent transcriptional elongation and Tat-P-TEFb association. To molecularly dissect UMB-136's effect on HIV-1 transcription, a protein pull-down assay was performed as previously described utilizing biotiny-lated UMB-136. The results showed that UMB-136 binds to endogenous BRD4 but not BRD2 (FIG. 2D). Furthermore, UMB-136 treatment resulted in greater protein association between P-TEFb (CCNT1) and Tat (FIG. 2E).

Figure 2F:
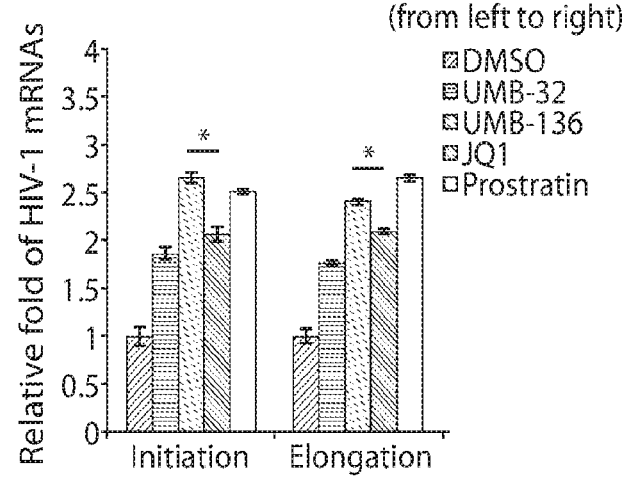
FIG. 2F shows that MB-136 enhanced viral production in full-length viral model, comparable to prostratin, while JQ1 did not.
Figure 2G:
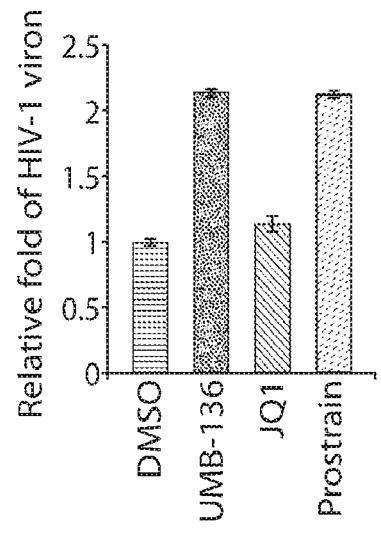
FIG. 2G shows relative fold of HIV-1 viron by UMB-136.

As BETis have been shown to increase HIV-1 transcription, it was desired to determine the effect of UMB-136 on HIV-1 transcription. This was tested in VSV-G pseudo-typed HIV-1 NL4-3-Luciferase virus infected Jurkat cells. By using qPCR assays to measure HIV-1 transcript length, it was found that UMB-136 enhances both transcriptional initiation and elongation of HIV-1 in, Jurkat cells, similar to prostratin (FIG. 2E). Furthermore, the experiment was repeated on full replication competent NL4-3 infected Jurkat cells in order to determine the effect of UMB-136 with respect to full replication. UMB-136 enhanced viral production in this full-length viral model, comparable to prostratin, while JQ1 did not (FIG. 2F). This is consistent with earlier studies, which showed that JQ1 alone does not enhance HIV-1 production in primary cell models.

Figures 1, 4A:
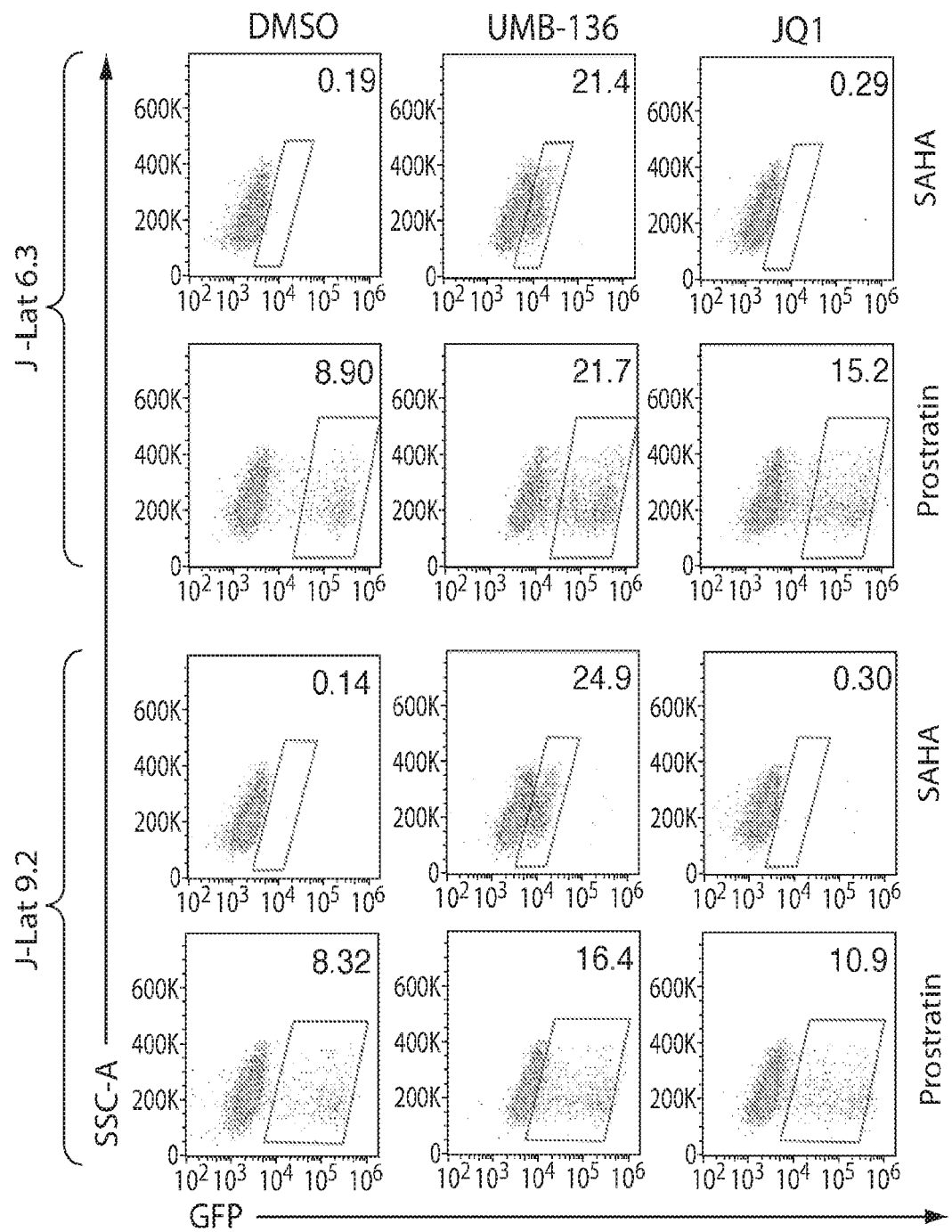
FIG. 4A (-1 and -2) shows that UMB-136 had a greater effect of HIV-1 reactivation than its JQ1 counterpart.
Figures 2, 4A:
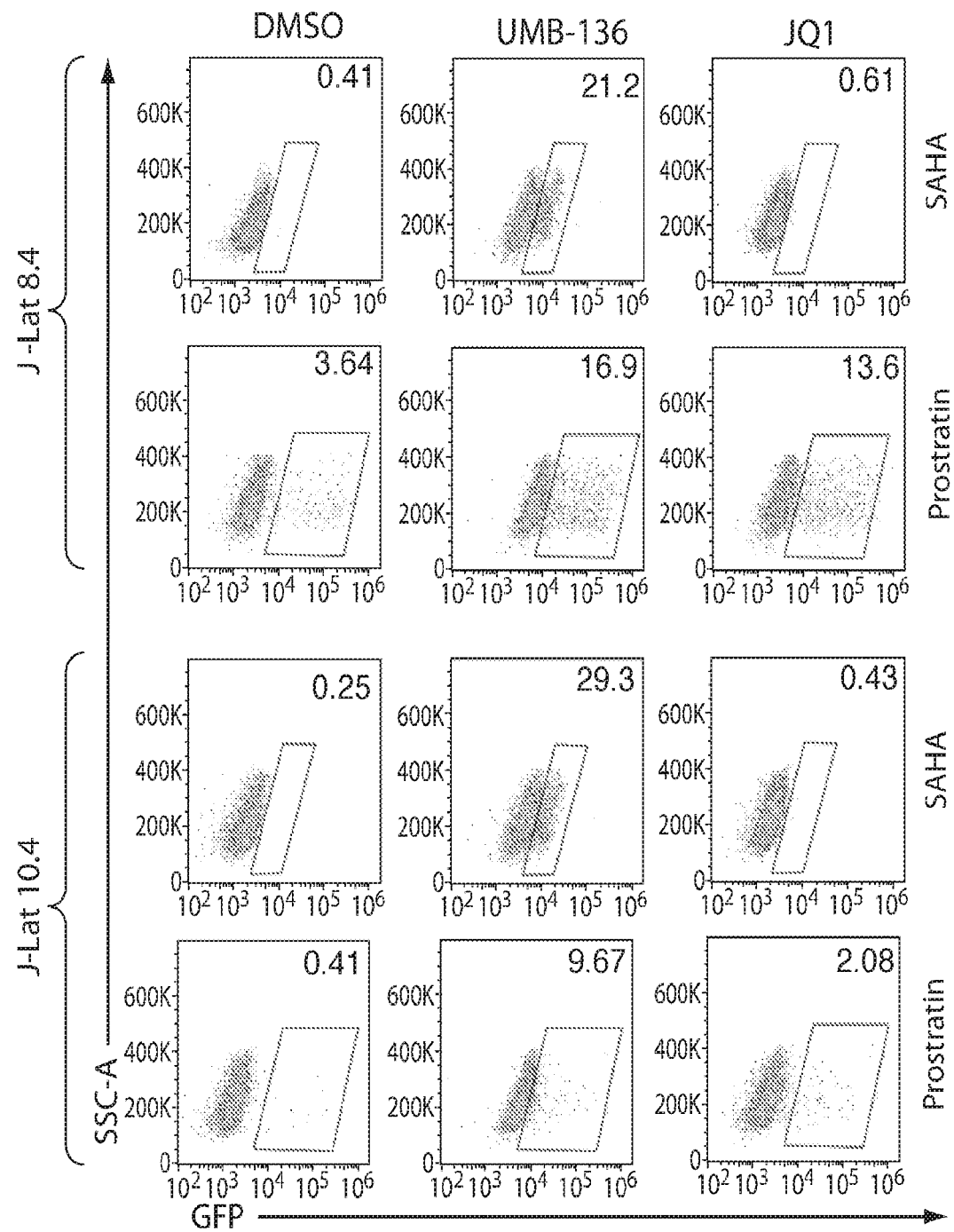

The data are summarized in FIG. 2. Results are presented as mean±s.e.m. of two or three biological replicates*, p<0.05, t-test.

Figure 3A:
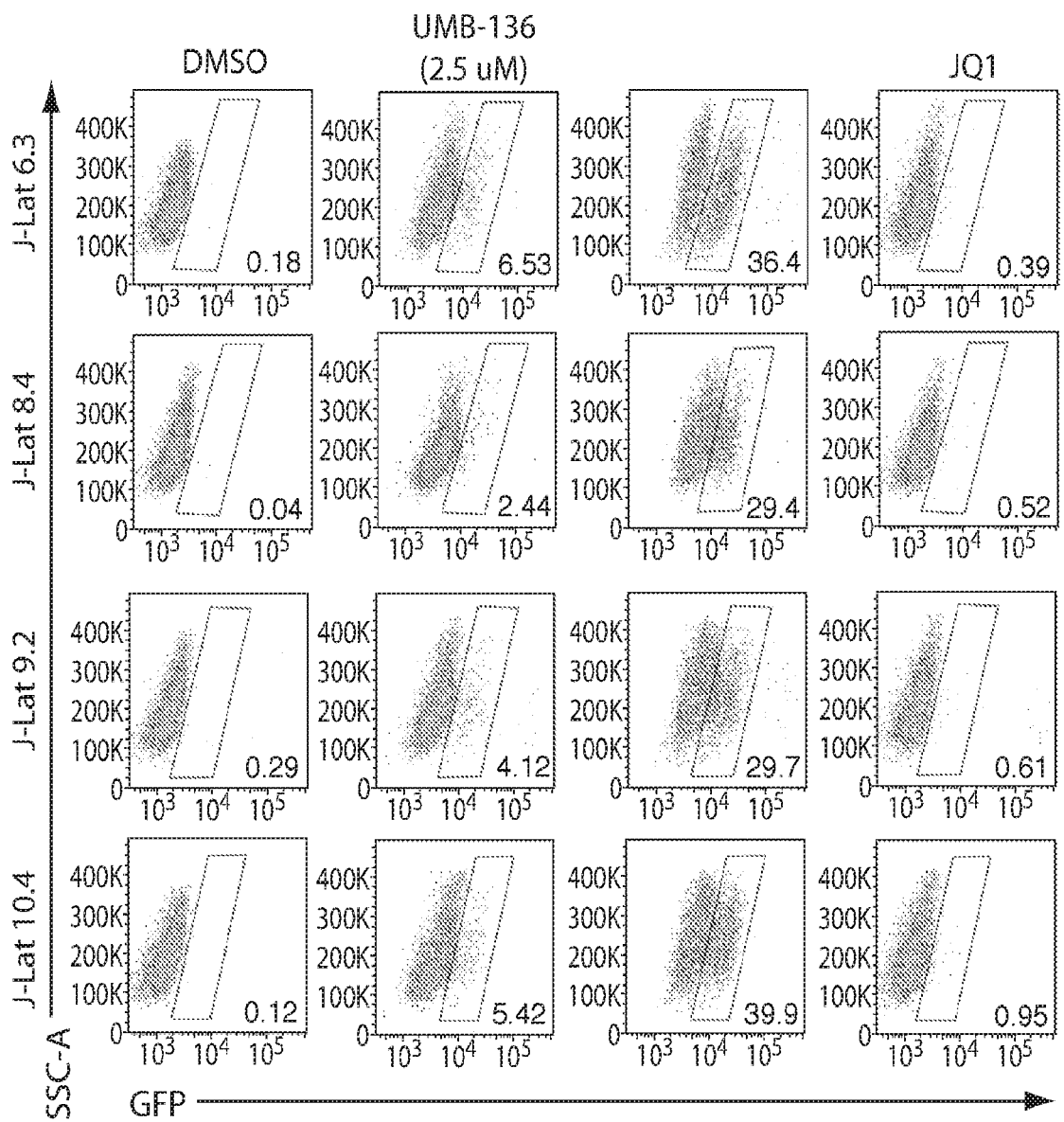
FIG. 3A shows results of flow cytometry on several J-Lat full-length (dEnv) clones (6.3, 8.4, 9.2, and 10.4) treated with indicated LRAs.
Figure 3B:
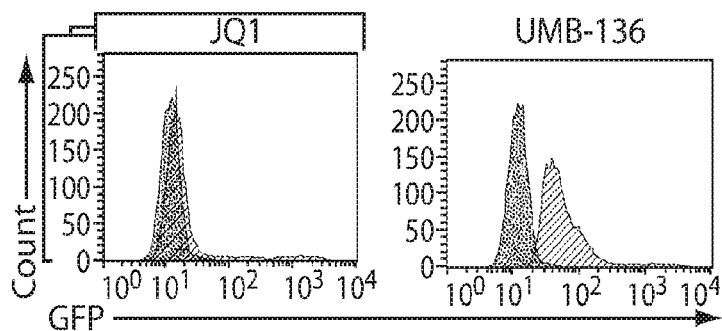
FIG. 3B shows that UMB-136 treatment of clones leads to substantial reactivation where JQ1 did not.
Figure 3C:
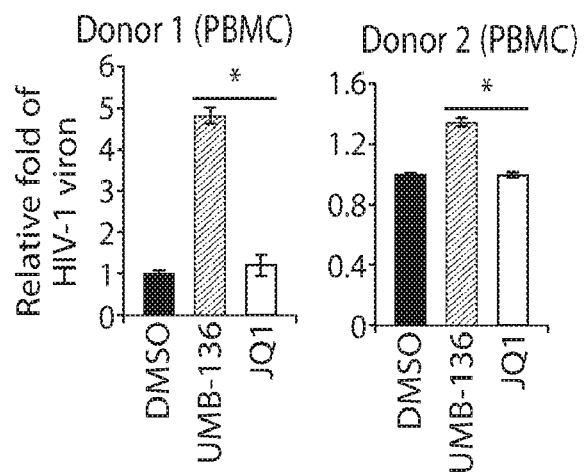
FIG. 3C shows that UMB-136 efficiently reactivated latent virus in non-polarized, memory CD4+ T cells isolated from either blood or lymph node.
Figure 3D:
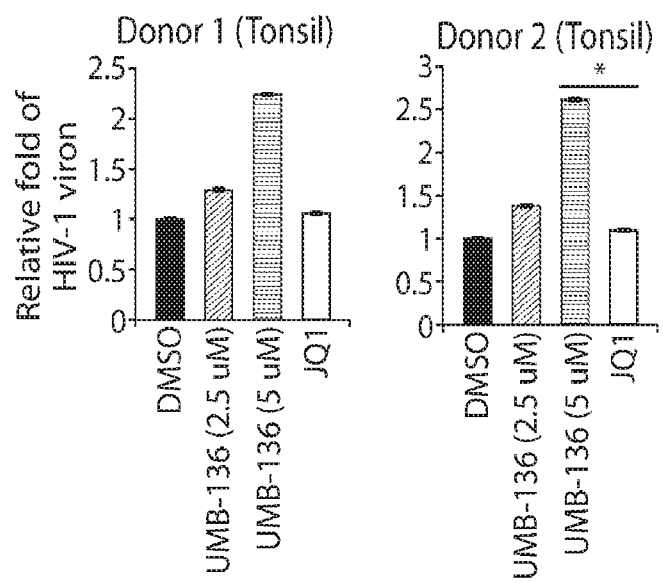
FIG. 3D shows that UMB-136 does not induce cytokine release in primary CD4+ T cells from healthy donor.

UMB-136 was Determined to Reverse HIV-1 Latency in Multiple Cell Models of HIV-1 Latency To fully determine the potential of UMB-136 in reactivating full-length HIV-1 genome in multiple cell models of HIV-1 latency, flow cytometry was performed on several J-Lat full-length (dEnv) clones (6.3, 8.4, 9.2, and 10.4) treated with indicated LRAs in FIG. 3A. UMB-136 treatment dramatically reversed HIV-1 latency at both low (2.5 PM) and high (5 PM) doses, while, consistent with previous studies, JQ1 elicited no observable effect. UMB-136 and JQ1 were also compared in THP89GFP cells, a previously described HIV-1 latency monocytic cell line containing a wild-type HIV-1 89.6 strain engineered to express GFP. UMB-136 treatment leads to substantial reactivation where JQ1 did not (FIG. 3B). To further evaluate the effect of UMB-136, a primary CD4+ T cell model of HIV-1 latency originally developed by Planelles' group was studied. As described above, naïve CD4+ T cells were isolated from peripheral blood mononuclear cells (PBMCs) or tonsillar mononuclear cells (TMCs) from two donors. Latency-reversing effects were determined by measuring the luciferase activity, which showed that UMB-136 efficiently reactivated latent virus in non-polarized, memory CD4+ T cells isolated from either blood or lymph node (tonsil) (FIG. 3C, D). It was also determined that UMB-136 does not induce cytokine release in primary CD4+ T cells from healthy donor.

The data are presented in FIG. 3. Results are presented as mean±s.e.m. (n=3); *, p<0.05, t-test.

Figure 4B:
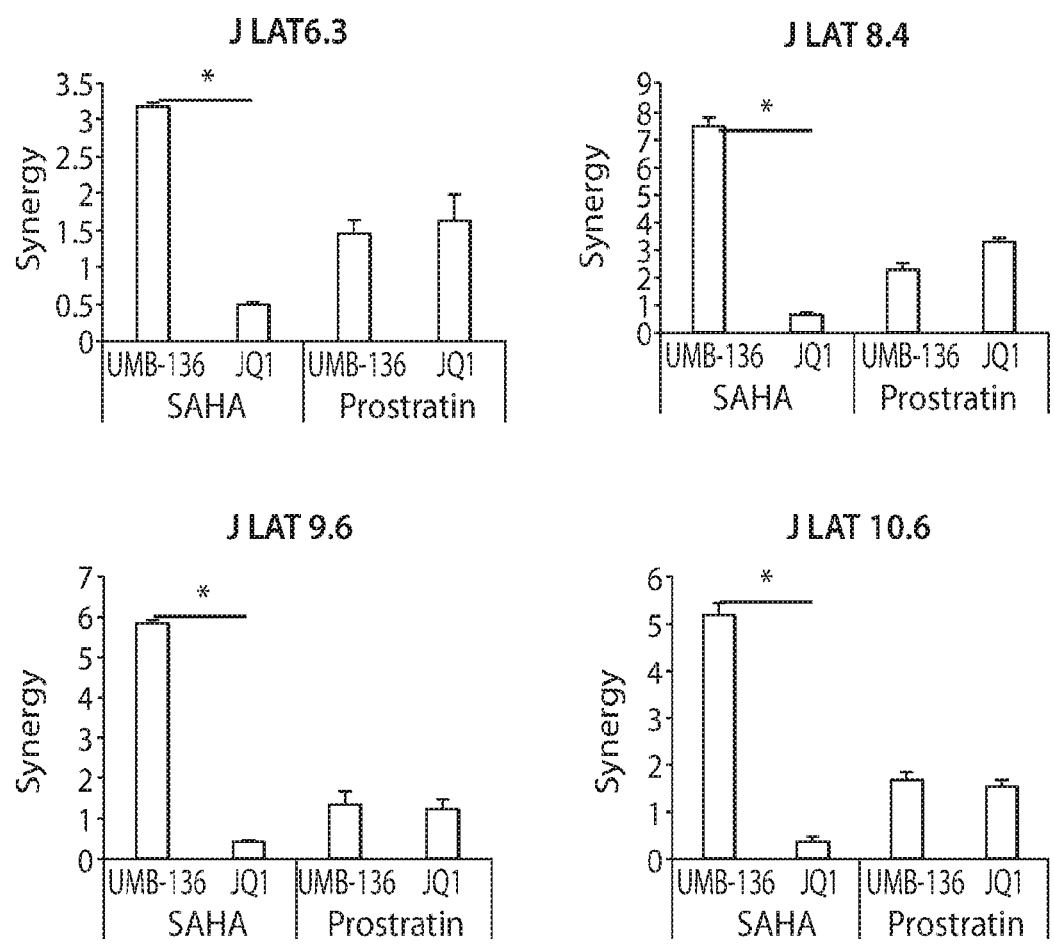
FIG. 4B UMB-136+SAHA and UMB-136+prostratin both yield a statistically significant synergistic effect in reversing HIV-1, while JQ1 only significantly synergizes with prostratin based on the Bliss independence model.
Figure 5A:
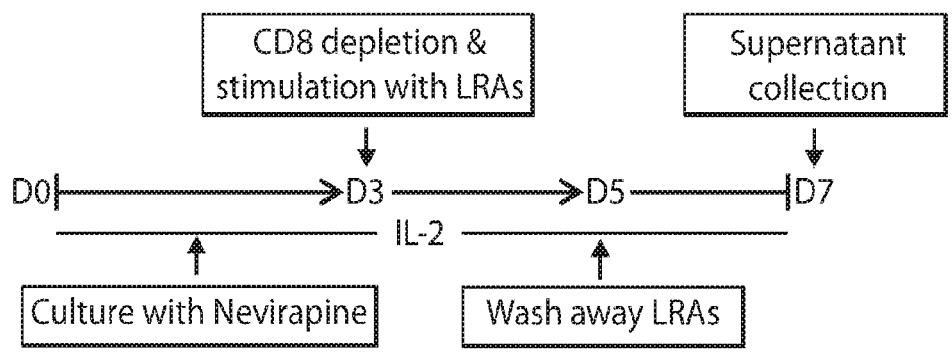
FIG. 5A shows an experimental scheme to observe reversal of HIV-1 latency by test compounds.

It was Determined that UMB-136 Synergizes with Other LRAs to Reverse HIV-1 Latency in Jurkat-Based Latency Models Recent studies show that a combination of BETis (JQ1) with other types of LRAs, specifically PKC agonists (prostratin, ingenol-B and bryostatin-1), is one of the most effective combinations to reactivate latent HIV-1 in reservoir cells. It is even comparable to stimulation using anti-CD3/ CD28 antibodies in some cases. Since UMB-136 when used as a single LRA showed better effect than JQ1 (FIG. 3), it was next studied whether UMB-136 would also exceed JQ1 when used in LRA combinations. Multiple J-Lat clones (6.3, 8.4, 9.2, and 10.4) were co-treated with UMB-136 (2.5 μM) or JQ1 in combination with vorinostat/SAHA, a histone deacetylation inhibitor (HDACi), or prostratin. In both combinations, UMB-136 had a greater effect of HIV-1 reactivation than its JQ1 counterpart (FIG. 4A). UMB-136+SAHA and UMB-136+prostratin both yield a statistically significant synergistic effect in reversing HIV-1, while JQ1 only significantly synergizes with prostratin based on the Bliss independence model (FIG. 4B). Data are represented in FIG. 4 as the mean±SD of biological duplicates*, p<0.05, t-test. It was Determined that Combined Treatment with UMB-136 and PKC Activators Reverses HIV-1 Latency in Patient-Derived Resting CD4+ T Cells LRA combinations of BETis (JQ1, UMB-136) and PKC agonists (prostratin, bryostatin-1) were evaluated ex vivo using CD8-depleted PBMCs isolated from multiple aviremic HIV-infected patients with an undetectable viral load (<50 copies/ml) and normal CD4 count (>300 cells/mm$^3$), as previously discussed herein. A combination of UMB-136 with PKC agonists (prostratin or bryostatin-1) was observed to reverse HIV-1 latency (FIG. 5A, B). Importantly, while JQ1 when used in combination with bryostatin-1 has been reported to potently reverse HIV-1 latency, UMB-136+bryostatin-1 notably elicited an even greater viral reactivation. To consider drug toxicity, cell death due to LRA treatments was measured. It was found that UMB-136 and prostratin/bryostatin-1 combinations generally result in less cytotoxicity than JQ1 and prostratin/bryostatin-1 combinations. Data are presented in FIG. 5. P values were shown as indicated, wilcoxon signed rank test.

The N-cyclohexyl group at position 3 of the imidazo[1,2-a] pyrazine in conjunction with the methoxy group position 2 of the benzene ring appear important in improving the potency of the parental UMB-32 (FIG. 1A). This hypothesis is supported by the predicted binding of UMB-136 to BRD4 BD1 with lower energy than UMB-32, assuming that UMB-136 occupies the active site of BRD4 BD1 with a similar binding pose as compared to UMB-32 (FIG. 2A). This allows conservation of all previously described interactions including: hydrogen bonding to surrounding asparagine and structural waters, and pi-stacking with tryptophan. Furthermore, the addition of cyclohexane and methoxy groups both enhance the binding, with the larger sized cyclohexane group replacing the t-Bu in UMB-32, and burying itself even deeper into the groove between the WPF shelf and the BC loop. The methoxy group, which is connected to the central phenyl ring, is very likely to bring in additional complementary integration or even hydrophobic interactions (FIG. 2B). These postulates are consistent with performed binding energy calculations (FIG. 2C). UMB-283, which significantly mimics the chemical structure of UMB-136, maintains a similar potency, reiterating the beneficial effect of the cyclohexane and methoxy groups.

BETis, as a new class of HIV-1 LRAs, are shown to facilitate the eradication of HIV-1 latent reservoirs. This observation may be due to the BETis driven release of sequestered P-TEFb and promotion of RNA pol-II activity at the HIV-1 LTR, which was confirmed for both JQ1 and UMB-136 (FIG. 2E). A thorough comparison showed that among first generation of BETis (JQ1, I-BET, I-BET151) tested to reverse HIV-1 latency, when combined with a PKC agonist (bryostatin-1) JQ1 is the most effective. However, JQ1 alone is inefficient to reverse viral latency in primary CD4+ T cell models or cART-treated HIV-1 aviremic patient's CD8 depleted PBMCs.

Figure 5B:
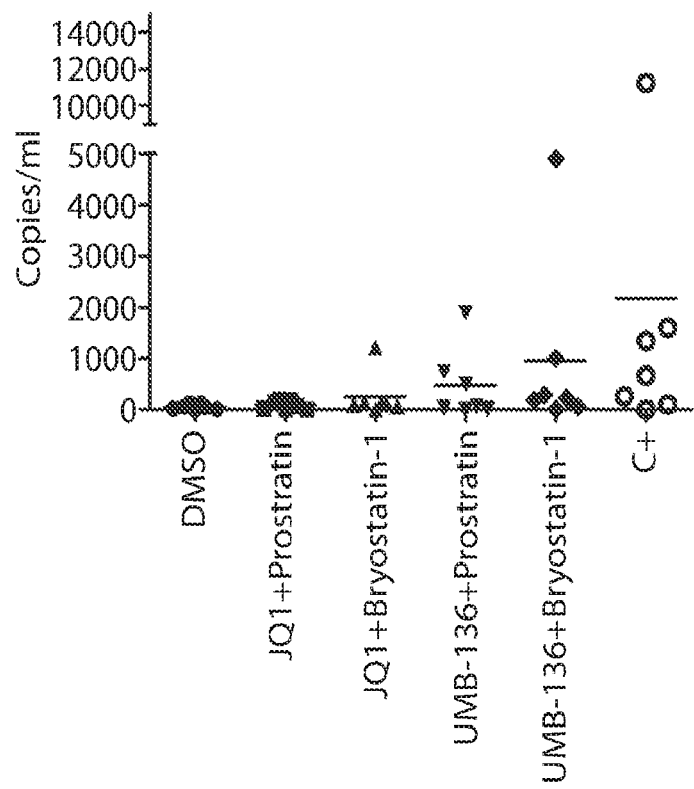
FIG. 5B shows that a combination of UMB-136 with PKC agonists (prostratin or bryostatin-1) was observed to reverse HIV-1 latency.

The results show that UMB-136 alone is capable of reversing latent HIV-1 in several J-Lat cell clones (FIG. 3A) as well as in monocytes harboring latent proviruses (FIG. 3B). Similarly, UMB-136 alone enables the reversal of HIV-1 latency in a primary CD4+ T cell model, while JQ1 fails to do so (FIG. 3C, D). Protein pull-down assays further support that UMB-136 induces reversal of viral latency through specific binding with BRD4 (FIG. 2D). However, an earlier report suggests that both BRD4, BRD2 are expected protein targets of JQ1 in reactivating latent HIV-1. It is a possibility that there may be some redundancy between BRD factors in regulating HIV-1 transcription, but given that the interaction of BRD4 and P-TEFb is well characterized it is postulated that BRD4 is the main player among BRD factors or that at least that they may affect HIV-1 transcription through P-TEFb. In terms of LRA combination, UMB-136 also leads to a greater effect of HIV-1 reactivation than JQ1, producing a synergistic effect when combined with HDACis (vorinostat/SAHA) or PKC agonists (prostratin) while JQ1+SAHA combination minimally reactivates latent HIV-1 in J-Lat cell clones (FIG. 4A). Similar results are observed in CD8-depleted PBMCs from cART-treated HIV-1 aviremic patients when cells are treated with either drug in combination with PKC agonists (bryostatin-1, prostratin) (FIG. 5B).

HIV-1 latency-reversing assays across multiple latency cell models, including a set of J-Lat clones, monocytes (THP89GFP), primary CD4+ T cells (FIGS. 3, and 4), demonstrate that UMB-136, whether alone or combined with other LRAs, is more potent than JQ1 in reactivating latent HIV-1. Meanwhile, it was observed that across different cell line models and ex vivo models, the effect of UMB-136 varies although it shows significant improvement when compared to JQ1. An in-depth comparison of latent HIV-1 reactivation in multiple cell model systems and resting CD4+ T cells from aviremic patients found that most cells models demonstrate skewed sensitivities towards or against specific drug classes used in HIV reactivation. However, even in primary CD4+ T cell models of HIV-latency, response to the same set of LRAs can be quite varied between models. Importantly, co-treatment with bryostatin-1 shows statistical significance between UMB-136 and JQ1 in aviremic samples (FIG. 5B). Earlier studies from two individual groups concluded that the combination of JQ1 with bryostatin-1 is one of the best LRA pairs to reverse HIV-1 latency, comparable to the positive control simulation (CD3/CD28 antibodies). Use of UMB-136 for such a therapy would lead to a better efficiency than JQ1.

The study also demonstrates the use of the HIV-1 latency-reversing assay as quick and convenient cell-based assay to evaluate the potency of new BETis. As this assay is independent of cell proliferation and growth assays, both of which are routinely used to test BETi-treated cancer cells, it is believed that it would be a valuable cross validation of drug effect for new BETis. This assay successfully identified a leading compound, UMB-136, from a set of UMB-32 analogs. Improved BETis, such as UMB-136 may be valuable for application in both anti-tumor and anti-HIV therapies.

While specific embodiments of the subject invention have been discussed, the above specification is illustrative and not restrictive. Many variations of the invention will become apparent to those skilled in the art upon review of this specification and the claims below. The full scope of the

The invention claimed is:
1. A compound selected from:

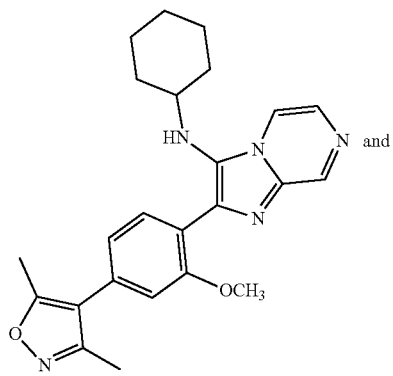

UMB136 and

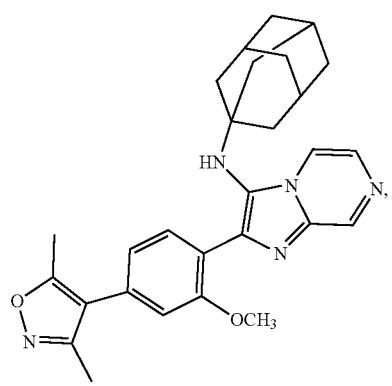

UMB283 or a pharmaceutically acceptable salt thereof.

2. A pharmaceutical composition, comprising:
a compound of claim 1, or a pharmaceutically acceptable salt thereof, and optionally a pharmaceutically acceptable excipient.

3. The pharmaceutical composition of claim 2, further comprising a second therapeutic agent.

4. The pharmaceutical composition of claim 2, comprising a therapeutically effective amount of the compound or pharmaceutically acceptable salt thereof.

5. The pharmaceutical composition of claim 2, formulated for oral administration to a subject.

6. The pharmaceutical composition of claim 2, wherein the composition is packaged for single use.

7. A method of treating a disease associated with a bromodomain-containing protein in a subject in need thereof, the method comprising:
administering to the subject a therapeutically effective amount of a compound of claim 1, or a pharmaceutically acceptable salt thereof.

8. A method of reactivating HIV latency in a subject, comprising:
administering to the subject a therapeutically effective amount of a compound of Formula (I):

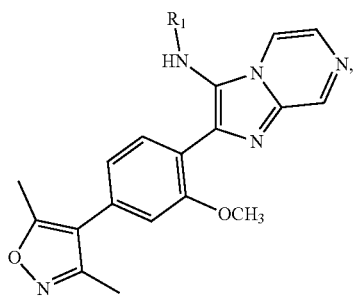

wherein $R_1$ is cycloalkyl, heterocycloalkyl or alkyl, or a pharmaceutically acceptable salt thereof.

9. A method of inhibiting activity of a bromodomain-containing protein in a subject, comprising:
administering to the subject a compound of claim 1, or a pharmaceutically acceptable salt thereof.

10. A method of treating HIV-1 disease in a subject in need thereof, the method comprising:
administering to the subject a therapeutically effective amount of a compound of Formula (I):

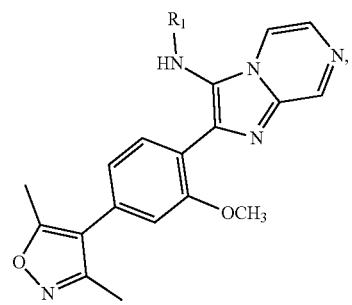

wherein $R_1$ is cycloalkyl, heterocycloalkyl or alkyl, or a pharmaceutically acceptable salt thereof.

11. The method of claim 10, wherein an amount and/or a frequency of administration is sufficient to treat HIV-1.

12. The method of claim 8, wherein an amount and/or a frequency of administration is sufficient to reactivate HIV latency in the subject.

13. The method of claim 10, wherein the subject is human.

14. The method of claim 10, wherein the compound is administered as part of a combination therapy.

15. The method of claim 12, wherein the compound is administered in combination with at least one Protein Kinase C (PKC) agonist to reactivate latent HIV-1.

16. The method of claim 10, wherein the compound is administered as an analgesic.

17. The method of claim 10, wherein the compound is administered as a prophylactic.

18. The method of claim 10, wherein the compound is self-administered.

19. The method of claim 10, wherein the compound is administered in response to a symptom of HIV-1.

20. A kit, comprising:
a compound of claim 1, or a pharmaceutically acceptable salt thereof; and
instructions for using the compound for treatment of a subject.

* * * * *